(12) United States Patent
West et al.

(10) Patent No.: US 11,413,394 B1
(45) Date of Patent: Aug. 16, 2022

(54) DISPLAY FOR WEARABLE DRUG DELIVERY DEVICE

(71) Applicant: Fresenius Kabi Deutschland GmbH, Bad Homburg (DE)

(72) Inventors: Sharon D. West, Elkins Park, PA (US); Jason Zerweck, Media, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/180,429

(22) Filed: Feb. 19, 2021

(51) Int. Cl.
*A61M 5/172* (2006.01)
*A61M 5/142* (2006.01)

(52) U.S. Cl.
CPC ........ *A61M 5/14248* (2013.01); *A61M 5/172* (2013.01); *A61M 2005/14252* (2013.01); *A61M 2205/583* (2013.01); *A61M 2205/587* (2013.01)

(58) Field of Classification Search
CPC ............ A61M 5/4244; A61M 5/14248; A61M 2005/14252; A61M 5/172; A61M 15/0071; A61M 60/585; A61M 2205/502; A61M 2205/505
See application file for complete search history.

(56) References Cited

U.S. PATENT DOCUMENTS

| | | | | |
|---|---|---|---|---|
| 4,970,502 A | * | 11/1990 | Kunikane | G09G 3/004 345/467 |
| 2003/0167036 A1 | | 9/2003 | Flaherty | |
| 2004/0068230 A1 | * | 4/2004 | Estes | A61M 5/14244 604/154 |
| 2012/0010594 A1 | | 1/2012 | Holt et al. | |
| 2015/0374919 A1 | | 12/2015 | Gibson | |
| 2016/0038689 A1 | | 2/2016 | Lee et al. | |
| 2016/0199574 A1 | | 7/2016 | Ring et al. | |
| 2016/0296704 A1 | | 10/2016 | Gibson | |
| 2016/0354555 A1 | | 12/2016 | Gibson et al. | |
| 2017/0119969 A1 | | 5/2017 | McCullough et al. | |
| 2017/0124284 A1 | | 5/2017 | McCullough et al. | |
| 2017/0147787 A1 | | 5/2017 | Albrecht et al. | |
| 2017/0182253 A1 | | 6/2017 | Folk et al. | |
| 2017/0340837 A1 | | 11/2017 | Nazzaro et al. | |
| 2017/0361015 A1 | | 12/2017 | McCullough | |

(Continued)

FOREIGN PATENT DOCUMENTS

EP 2242034 A1 * 10/2010 ............. G09F 11/00
WO 2018081234 A1 5/2018
(Continued)

*Primary Examiner* — Quynh-Nhu H. Vu
(74) *Attorney, Agent, or Firm* — Cook Alex Ltd.

(57) ABSTRACT

A drug delivery device has a housing including upper and lower surfaces, with an adhesive pad associated with the lower surface of the housing and configured to removably attach to a human body surface. A drug reservoir is positioned within the housing, with a needle fluidically connected to the drug reservoir and configured to define at least a portion of a fluid flow path between the drug reservoir and said human body surface. A controller is configured to control the components of the drug delivery device to execute a drug delivery routine, with a display coupled to the controller and configured to receive signals from the controller so as to provide an indicium visible through the upper surface of the housing. The display may be electrical or mechanical in nature.

17 Claims, 5 Drawing Sheets

(56) References Cited

U.S. PATENT DOCUMENTS

| | | |
|---|---|---|
| 2017/0368260 A1 | 12/2017 | McCullough et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0256823 A1 | 9/2018 | Nazzaro et al. |
| 2018/0272059 A1 | 9/2018 | Marbet et al. |
| 2018/0304014 A1 | 10/2018 | Knudsen et al. |
| 2019/0022306 A1 | 1/2019 | Gibson et al. |
| 2019/0050375 A1 | 2/2019 | Fitzgibbon et al. |
| 2019/0060562 A1 | 2/2019 | Olivas et al. |
| 2019/0083702 A1 | 3/2019 | Nekouzadeh et al. |
| 2019/0134296 A1 | 5/2019 | Barbedette et al. |
| 2019/0143043 A1 | 5/2019 | Coles et al. |
| 2019/0143047 A1 | 5/2019 | Jazayeri et al. |
| 2019/0151544 A1 | 5/2019 | Stonecipher |
| 2019/0167908 A1 | 6/2019 | Fitzgibbon et al. |
| 2019/0192766 A1 | 6/2019 | Stonecipher |
| 2019/0247579 A1 | 8/2019 | Damestani |
| 2019/0275241 A1 | 9/2019 | Ring et al. |
| 2019/0328965 A1 | 10/2019 | Moberg |
| 2019/0365986 A1 | 12/2019 | Coiner et al. |
| 2019/0374707 A1 | 12/2019 | Damestani et al. |
| 2019/0381238 A1 | 12/2019 | Stonecipher et al. |
| 2020/0023122 A1 | 1/2020 | McCullough et al. |
| 2020/0164145 A1 | 5/2020 | Chang et al. |
| 2020/0164155 A1 | 5/2020 | Mojarrad et al. |
| 2020/0179609 A1 | 6/2020 | Tan-Malecki et al. |
| 2020/0197628 A1 | 6/2020 | McCullough et al. |
| 2020/0206429 A1 | 7/2020 | Hering et al. |
| 2020/0230313 A1 | 7/2020 | Mojarrad et al. |
| 2020/0238004 A1 | 7/2020 | McCullough |
| 2020/0254172 A1 | 8/2020 | Forster et al. |
| 2020/0261648 A1 | 8/2020 | Groszmann et al. |
| 2020/0261657 A1 | 8/2020 | Gibson et al. |
| 2020/0289745 A1 | 9/2020 | Harris et al. |
| 2020/0297927 A1 | 9/2020 | Conrath et al. |
| 2020/0322793 A1 | 10/2020 | Yang |
| 2020/0338271 A1 | 10/2020 | Harris et al. |

FOREIGN PATENT DOCUMENTS

| | | |
|---|---|---|
| WO | 2018183039 A1 | 10/2018 |
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

* cited by examiner

DISPLAY FOR WEARABLE DRUG DELIVERY DEVICE

BACKGROUND

Field of the Disclosure

The present disclosure relates to drug delivery devices. More particularly, the present disclosure relates to improved displays for devices mounted to the body for automatically delivering a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

Figure 1:
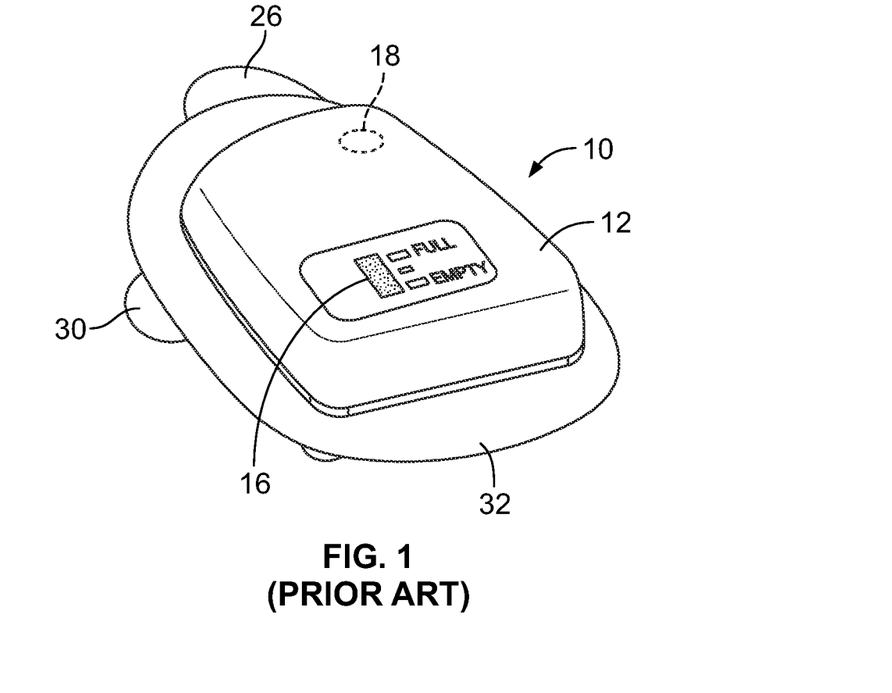
FIG. 1 is a top perspective view of a drug delivery device according to conventional design.
Figure 2:
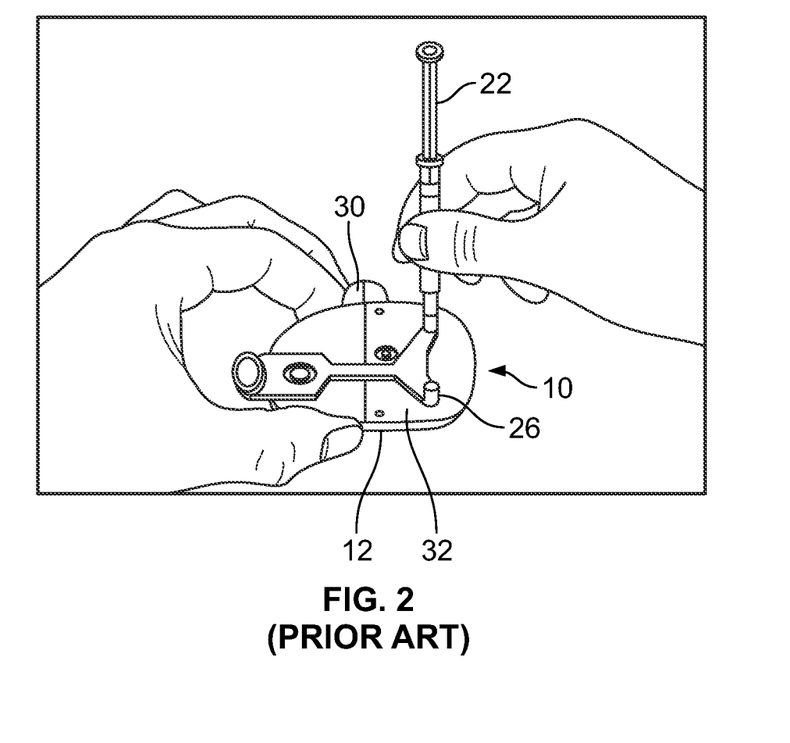
FIG. 2 is a bottom perspective view of the drug delivery device of FIG. 1.
Figure 3:
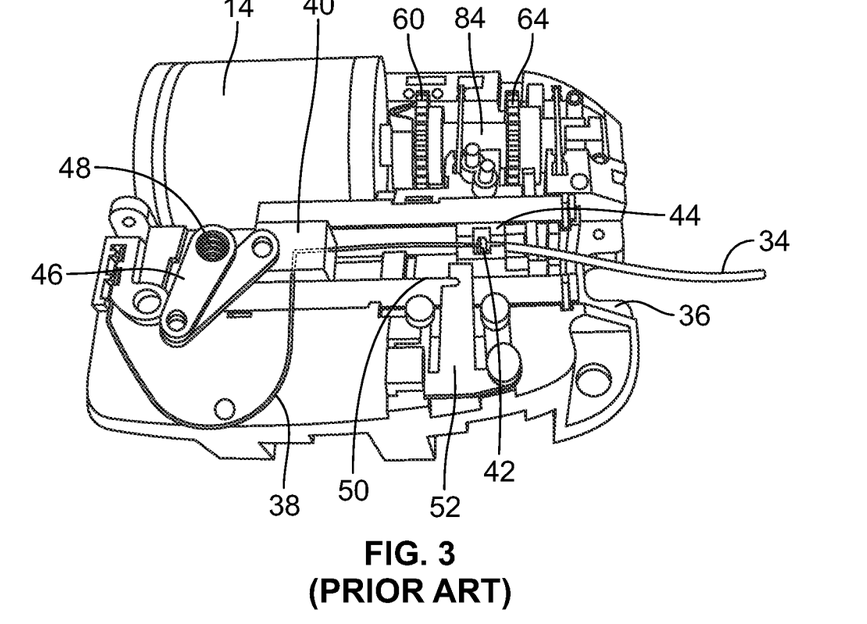
FIG. 3 is a top perspective view of the interior components of the drug delivery device of FIG. 1.
Figure 4:
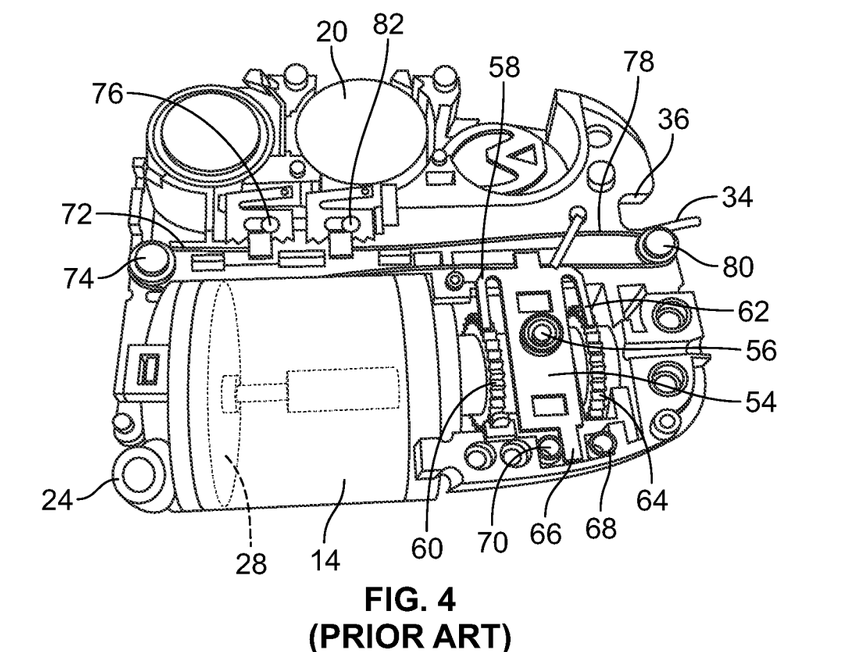
FIG. 4 is a bottom perspective view of the interior components of the drug delivery device of FIG. 1.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, the display of the device and information relayed to the user can be greatly improved. Although basic information can be provided, such as whether the device is attached correctly, it is important to provide more detailed feedback to the user.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a drug delivery device comprises a housing including upper and lower surfaces, an adhesive pad associated with the lower surface of the housing and configured to removably attach to a human body surface, a drug reservoir positioned within the housing, a needle fluidically connected to the drug reservoir and configured to define at least a portion of a fluid flow path between the drug reservoir and said human body surface. The drug delivery device also includes a controller configured to control the components of the drug delivery device to execute a drug delivery routine and a display electrically coupled to the controller and configured to receive signals from the controller so as to provide an indicium visible through the upper surface of the housing. The display includes electronic ink and/or an organic light-emitting diode array.

In another aspect, a drug delivery device includes a housing with upper and lower surfaces; an adhesive pad associated with the lower surface of the housing and configured to removably attach to a human body surface; a drug reservoir positioned within the housing; a needle fluidically connected to the drug reservoir and configured to define at least a portion of a fluid flow path between the drug reservoir and said human body surface; a controller configured to control the components of the drug delivery device to execute a drug delivery routine; and a movable display positioned within the housing. The upper surface of the housing defines an overlay. The controller is configured to control the movable display to move with respect to the overlay from a first position to a second position. At least a portion of the movable display is visible through the overlay when the movable display is in one of said positions and said at least a portion of the movable display is differently visible or invisible through the overlay when the movable display is in the other one of said positions.

In another aspect, a drug delivery device includes a housing with upper and lower surfaces; an adhesive pad associated with the lower surface of the housing and configured to removably attach to a human body surface; a drug reservoir positioned within the housing; a needle fluidically connected to the drug reservoir and configured to define at least a portion of a fluid flow path between the drug reservoir and said human body surface; a controller configured to control the components of the drug delivery device to execute a drug delivery routine; and a movable display positioned within the housing. A flexible or deformable cover layer is associated with the upper surface of the housing. The controller is configured to control the movable display to move with respect to the cover layer from a first position in which the display engages and deforms the cover layer and a second position in which the display differently engages and deforms or does not deform the cover layer.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 5:
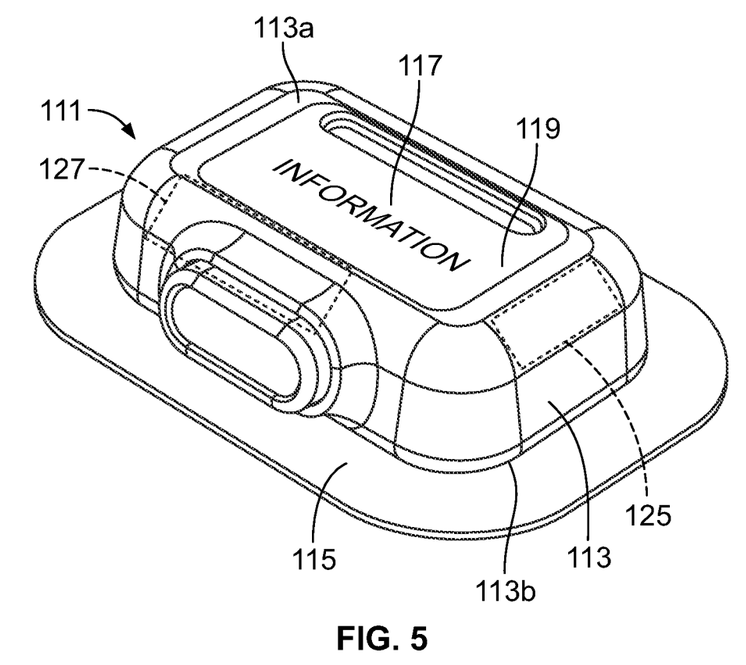
FIG. 5 is a top perspective view of an exemplary embodiment of a drug delivery device with an improved display, according to an aspect of the present disclosure.

FIG. 5 shows an exemplary drug delivery device 111 embodying aspects of the present disclosure. The drug delivery device 111 includes a housing 113 with an upper surface 113a and lower surface 113b. The housing 113 contains or encloses the functional components of the device 111, including a controller 125 and reservoir 127. The reservoir 127 is configured to be filled with a liquid drug to be delivered to the patient. The methods and devices described herein may be used to deliver any suitable fluid medication to a subject. In an exemplary embodiment, the methods and devices described herein are used to deliver pegfilgrastim to a subject, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin. There is also a needle (not shown) fluidically connected to the drug reservoir and configured to define at least a portion of a fluid flow path between the drug reservoir and a user. The housing 113 has an adhesive pad 115 associated with its lower surface 113b and configured to removably attach to a human body surface. The adhesive can be a pressure sensitive adhesive, particularly any medical grade pressure sensitive adhesive. The adhesive can be rubber, acrylic, and/or silicone based.

The controller 125 is configured to control the components of the drug delivery device 111 to execute a drug delivery routine. The controller may include a microprocessor (which, in fact may include multiple physical and/or virtual processors) and one or more electrical circuits and memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessor to carry out one or more actions as described below.

The controller 125 may be coupled (i.e., directly or indirectly connected) to the components of the device, such as the needle and reservoir. The controller may operate each of these components, each of which may be an assembly of other devices or equipment, to execute a drug delivery routine. The controller may be programmed to perform other actions as well. The controller is also coupled to a display 119 and sends signals to the display so that the display can notify the user of the device status, as will be described in greater detail herein.

The device 111 can also include buttons or icons associated with the controller. The buttons or icons may be variously configured and positioned at any suitable location of the device. The device may include two buttons or icons. One button/icon may be a start button/icon for initializing a procedure and the other button/icon of the set may be a stop button/icon for stopping a procedure.

The device 111 may also include at least one indicium 117 associated with the upper surface of the housing. The indicium is configured to provide information to a user, which may include for example an indication that the device is ready to begin a drug delivery procedure, that the device is performing a drug delivery procedure, that the device has completed a drug delivery procedure, and/or that there has been an error. The indicium may display or represent the status of the device in any suitable manner. For example, in one embodiment, an indicium may be configured as a shortened message that can display different words, and it may include colors and/or lights to further indicate the state of the device. The indicium may utilize any other type of indication known in the art without departing from the scope of the present disclosure.

The indicium is provided by operation of the display 119, which may be variously configured to provide information to the user. FIGS. 5-10 illustrate exemplary embodiments with different display configurations. Similar components are numbered similarly throughout the Figures.

The display can be electrical or mechanical in nature, with an electrical display configured to employ electrical means (e.g., electronic ink or organic light-emitting diode arrays) to create an indicium. On the other hand, a mechanical display includes one or more components that are physically moved so as create an indicium, and can be provided in combination with a housing having one or more portions through which a movable component is differently visible or perceptible when the component is in different positions within the housing. It is also within the scope of the present disclosure for a display to be both electrical and mechanical in nature, with at least one indicium being presented via electrical means and at least one indicium be presented via mechanical means.

If the display 119 is electrical in nature, as in the embodiment of FIG. 5, it may include a plurality of layers, with each performing a different specialized function. The display may alternatively include a single layer. In either case, the display can be associated or incorporated into to an inner or outer surface of the upper surface 113a of the housing. This may include one layer of a multi-layer display being associated to an outer surface of the upper surface of the housing (i.e., positioned outside of the housing), with another layer being associated to an inner surface of the upper surface of the housing (i.e., positioned within the housing).

An electrical display may include at least one layer of electronic ink. The ink can be a conductive ink and may also include conductive particles or capsules. The ink layer can be directly disposed on the upper surface of the housing of the device. The ink layer may also be disposed on different surfaces of the body of the device. The display may also include multiple layers of electronic ink. The ink layer or layers may be a single color (i.e., grayscale, with the binary state of an array of micro-miniature beads being changed by application of an electrical charge to show either black or white sides) or multiple colors.

An electronic ink display may also include a number of additional layers associated with the ink layer. Additional layers can include a support layer. The electronic ink display may also include at least one electrode layer. The electronic ink layer may also be attached to a plastic film.

An electrical display can alternatively (or additionally) include an organic light-emitting diode array. The OLED display may be composed of a number of layers. The OLED display includes at least one layer, an emissive layer. The OLED layer or layers can be disposed on the upper surface of the housing. The emissive layer can be comprised of organic material. The organic material can be at least one of a small organic molecule or organic polymer. The organic material can be at least one of polyfluorenes, phosphorescent metal complexes, vinyl carbazoles, poly(p-phenylene vinylene). The organic material can be electrically conductive. The OLED display can include more than one emissive layer, with additional layers providing increased efficiency.

The OLED display may further include at least one electrode layer. In one embodiment, the OLED display includes a cathode and anode layer. The cathode layer can include a metal such as barium or calcium. The anode layer can include an oxide, particularly indium tin oxide.

The OLED display may also include a substrate layer. The substrate can include glass, a sapphire, polymethyl methacrylate (PMMA), and polycarbonate (PC) or a combination thereof.

Regardless of the particular configuration of an electrical display, it should be understood that the indicium presented by such a display may be more informative than the display of a conventional drug delivery device. For example, rather than simply indicating that the device is ready for operation, is executing a drug delivery procedure, or is experiencing an error, an electrical display according to the present disclosure may indicate the exact nature of an error or more detailed information regarding an in-process procedure (e.g., the time remaining or the current stage of the procedure).

As for a mechanical display, it will typically include three primary components: one or more movable components or portions that are movable from a first position to a second position to provide an indicium, an adjustment mechanism that is controlled by the controller to move the movable component(s), and a portion of the upper surface of the housing through which the movable component is differently visible or perceptible when in the first and second positions so as to present said indicium.

The movable portion can include various movable pieces/components at least partially positioned within the housing of the device. The movable portion is at least movable from a first position to a second position (with it being differently visible or perceptible, including being invisible or imperceptible, in the two positions), but may be movable between the first and second positions. The movable portion may further be moved into additional positions without departing from the scope of the present disclosure, with the movable portion being different visible or perceptible in the different positions to provide different indicia in each position. The movable portions can have indicium (e.g., shapes or colors or printed text or symbols) and can include full messages, such as "in progress." Indeed, the movable portion may be provided in an extremely wide variety of configurations to present any of a number of possible indicia to a user.

Similar to the movable portion, the adjustment mechanism of a mechanical display may be provided in an extremely wide variety of configurations to impart different types of movement to the movable portion. Due to this wide variety of possible configurations, the adjustment mechanisms of FIGS. 6-10 (labeled as 229, 329, 429, and 529) are illustrated generically, with the understanding that many differently configured mechanisms may be employed to impart similar or different types of movement (e.g., translational, pivotal, or rotational movement).

By way of example, the adjustment mechanism may be electromechanically actuatable, utilizing electrical, pneumatic, or hydraulic fluid pressure energy. In one embodiment, the adjustment mechanism may comprise a screw, which may be variously configured without departing from the present disclosure, such as being configured as a lead-screw, screw jack, ball screw, roller screw, or linear rail actuators (for example). The adjustment mechanism may employ an electro-mechanical screw actuator with an associated motor that is actuated to move the screw and the movable portion of the display. In such an embodiment, the motor is driven in a forward direction to rotate the electro-mechanical screw actuator in a first direction (e.g., a clockwise direction), which causes corresponding movement of the screw and display in a first direction with respect to the housing (e.g., in a vertically downward direction). When the motor is driven in a reverse direction, it will cause the electro-mechanical screw actuator to rotate in the opposite direction (e.g., in a counterclockwise direction), which causes corresponding movement of the screw and movable component in a second direction (e.g., in a vertically upward direction).

In another exemplary embodiment, the adjustment mechanism may comprise an axle and a connection member. The connection member can be flexible or rigid and can be a chain, belt or cable or a rod or shaft. A motor drives in a forward direction to rotate the axle in a first direction and move the movable portion of the display in a first direction, and with the motor being driven in a reverse direction to rotate the axle and move the movable portion of the display in second direction that is opposite to the first direction.

In yet another exemplary embodiment, the adjustment mechanism can comprise a cam and a motor which is driven in forward and reverse directions to rotate the cam in opposite directions, thereby moving the movable portion of the display in opposite directions.

The adjustment mechanism may include a cylinder. In such an embodiment, the cylinder may be hollow and contain a piston that is configured to move through the cylinder. Such an adjustment mechanism also includes a fluid supply reservoir that fluidically communicates with the cylinder. The reservoir contains a fluid that may be alternately conveyed to and withdrawn from the cylinder in order to vary the pressure within the cylinder above the piston. As pressure in the cylinder above the piston increases the piston may move downwardly, causing the movable portion of the display to lower. As pressure in the cylinder above the piston decreases the piston moves upwardly, causing the movable portion of the display to rise. The cylinder and the piston may also operate in the opposite way.

The adjustment mechanism may alternatively (or additionally) include a magnetic linear motor. In such an embodiment, the motor includes a forcer containing a plurality of electromagnetic coils, with a plurality of aligned disk magnets passing through the centers of the electromagnetic coils. The disk magnets are arranged in an alternating pattern, with the north pole of each disk magnet facing the south pole of a first adjacent disk magnet and the south pole of each disk magnet facing the north pole of a second adjacent disk magnet. The motor operates as a conventional magnetic linear motor, with a magnetic force being applied to cause the forcer to move along an axis defined by the disk magnets. Movement of the forcer causes corresponding movement of the movable portion of the display.

In another embodiment, the adjustment mechanism may include a telescoping member. The telescoping member may comprise a flat band arranged in a helix, which may move between a collapsed condition and an elongated or extended condition. In the collapsed condition, adjacent turns of the band rest against each other or are spaced closely together, while the adjacent turns of the band are more greatly spaced apart in the extended condition (or a partially extended condition) for a greater height or length. As the band is moved from its collapsed condition to its extended condition, a second helical band is applied between the adjacent turns of the first band to occupy the space between the adjacent turns of the first band to provide stability to the resulting cylinder. As the first band is moved from its extended condition to its collapsed condition, the second band is removed from between the adjacent turns of the first band to allow the first band to fully or partially collapse. The second band (or at least the portion thereof that has not been applied between adjacent turns of the first band) is stored radially outwardly of the first band, allowing for the telescoping member to have a small profile when the first band is in its collapsed condition. Moving the telescoping member between its collapsed and extended conditions will cause movement of the movable portion of the display.

The adjustment mechanism may include a piezoelectric member, which is at least partially comprised of one or more materials designed to expand or contract with the application of electrical voltage. As voltage is applied to or removed from the piezoelectric member, it will alternately expand or contract. The piezoelectric member is associated with different components of the movable portion of the display, such that expansion and contraction of the piezoelectric member will cause the one or more of the movable components (or a portion thereof) to move.

The adjustment mechanism may also include a shape memory alloy. For example, at least one shape memory alloy can be associated with a movable portion of the display. The shape memory alloy may be deformed or reformed upon the application or removal of heat. This deforming or reforming may adjust or move the movable components of the display. In one embodiment, a first shape memory alloy can be used to pull or adjust a movable portion of the display from a first position to a second position. The deforming and reforming of the shape memory alloy can allow for movement between the two positions. Additionally, a second shape memory alloy can also be used to adjust the movable portion of the display from the second position back to the first position. The shape memory alloy may also be used in conjunction with another adjustment mechanism, such as a spring. In such an embodiment, the shape memory alloy may be utilized as an actuator, acting upon the other adjustment mechanism to actuate a change from one position to another position.

It should be understood that the foregoing adjustment mechanisms are merely exemplary and that other mechanisms may be employed without departing from the scope of the present disclosure. It is also contemplated that a single mechanical display may include two or more differently configured adjustment mechanisms to move different movable components of the display.

Figure 6:
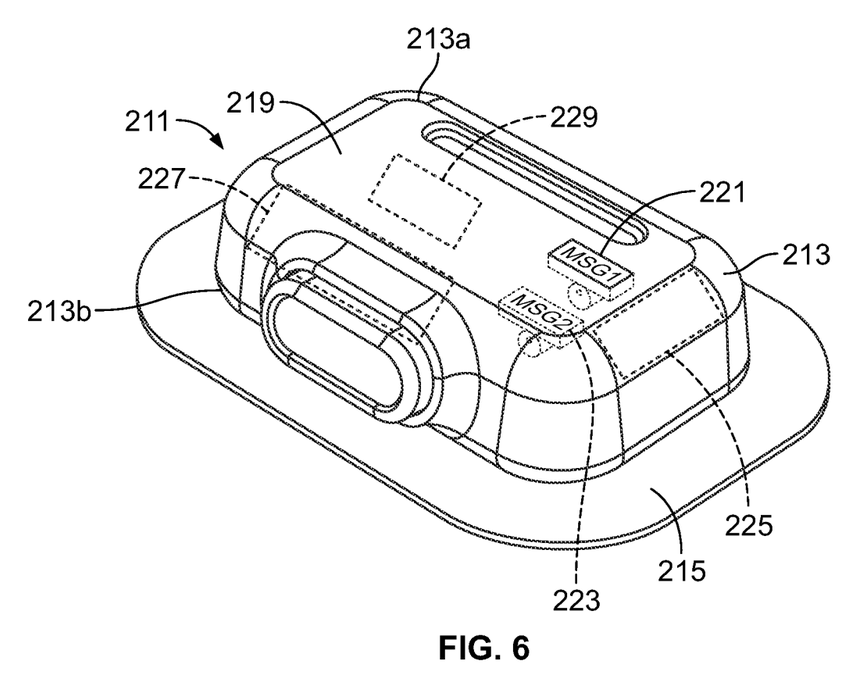
FIG. 6 is a top perspective view of another exemplary embodiment of a drug delivery device with an improved display, according to an aspect of the present disclosure.
Figure 7:
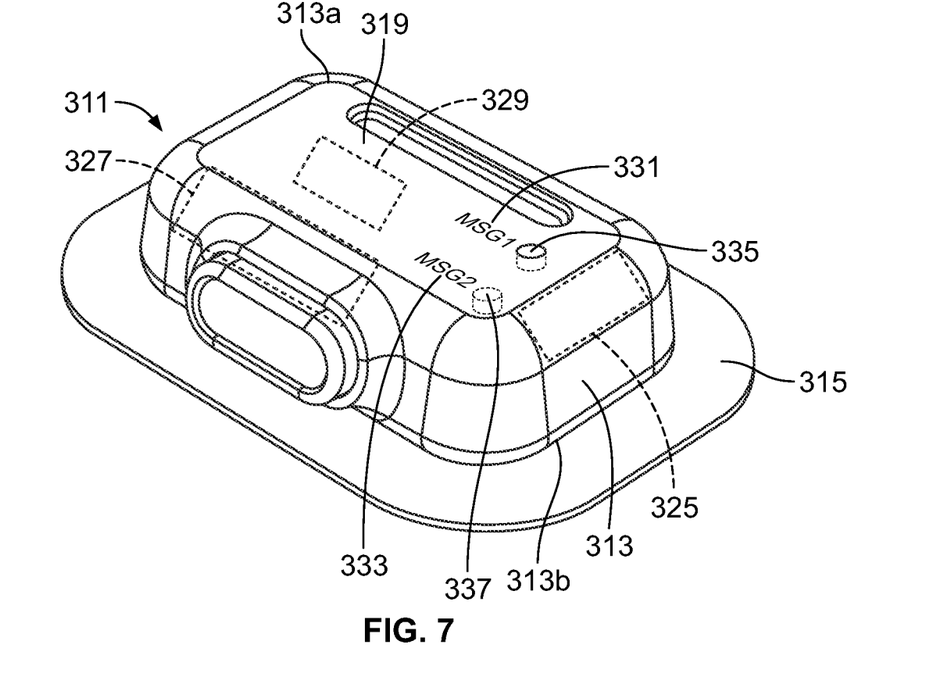
FIG. 7 is a top perspective view of a third exemplary embodiment of a drug delivery device with an improved display, according to an aspect of the present disclosure.
Figure 8:
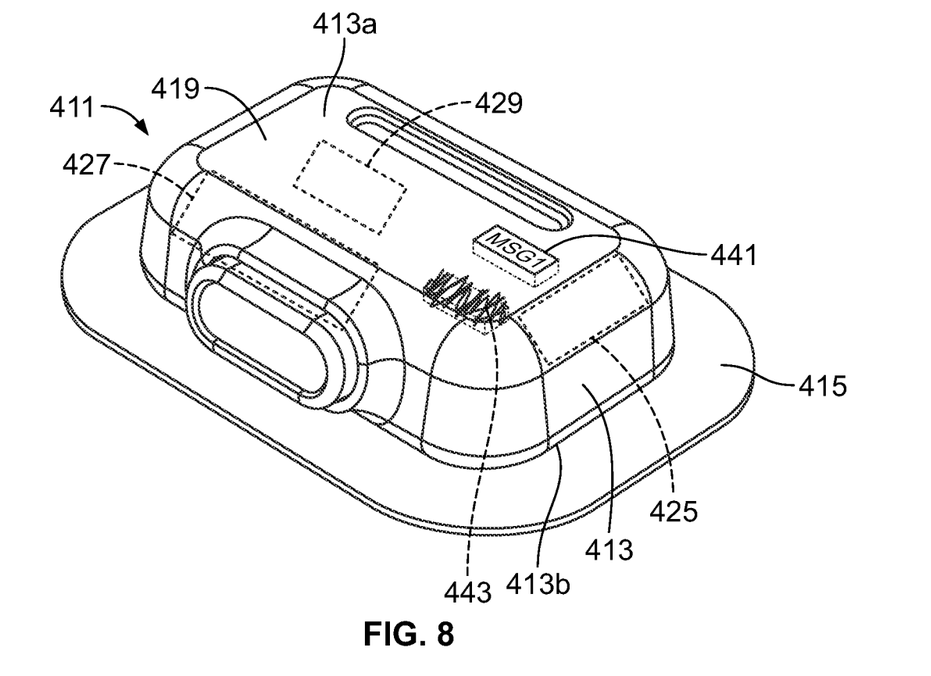
FIG. 8 is a top perspective view of a fourth exemplary embodiment of a drug delivery device with an improved display, according to an aspect of the present disclosure.

As noted above, in addition to the movable portion and the adjustment mechanism, the display also includes a portion of the upper surface of the housing of the device through which at least a portion of the movable component is differently visible or perceptible. FIGS. 6-8 illustrate such a component as an at least partially translucent or transparent window or overlay, typically formed of a generally rigid material to display different indicia. This portion of the upper surface of the housing can also (or alternatively) include a cover layer that deforms based on movement of components (as in FIGS. 9 and 10), with different deformations representing different indicia. The overlay or cover layer (collectively referred to herein as the "permanently visible portion" of the display) may be a translucent or "deadfront" display incorporated into or otherwise associated with the upper surface of the housing of the device. The permanently visible portion may either be blank or include one or more permanent indicia (e.g., printed text or symbols), which are always visible or perceptible regardless of the positions of the movable components of the display.

Turning now to exemplary embodiments of a mechanical display, FIG. 6 shows a display with an overlay 219. There are at least two movable components 221 and 223, each of which may include an indicium for the user. The movable components can be any shape or size (including being the same size and shape or differently configured), customizable to the shape/size of the indicium. Components 221 and 223 are shown in different positions, with component 221 being in a raised position, adjacent to the overlay 219 and visible therethrough, while component 223 is in a lowered position, spaced away from and not visible through the overlay 219. However, as described above, it should be understood that these components will be moved by respective adjustment mechanisms based on signals from the controller (which may be based on the status of the device), with component 221 being moved to a lowered or less visible position and component 223 being moved to a raised or more visible position. While components 221 and 223 are shown and described above with only one being visible through the overlay 219 at a time (to present different indicia), it is also possible for the components 221 and 223 to be moved such that both or neither are visible through the overlay 219 to provide additional, different indicia.

The display of FIG. 7 is similarly configured to the display of FIG. 6, but with components 335 and 337 that are smaller than those shown in FIG. 6 (which are shown with printed indicia), thus taking up a smaller portion of the overlay 319. On account of the components 335 and 337 taking up less space, the overlay 319 is shown with permanent indicia 331 and 333, which are positioned adjacent to the regions in which movable components 335 and 337 are positioned (when visible), respectively. As described above with regard to the embodiment of FIG. 6, the movable components 335 and 337 may be moved into positions so as to be individually visible, into positions in which both are visible, and into positions in which neither is visible, based on the status of the device and the information to be relayed to the user.

FIG. 8 shows another exemplary embodiment of a device that has a mechanical display with movable components. As in the embodiments of FIGS. 6 and 7, depending on their current position, movable components 441 and 443 can be visible through overlay 419 for select indicia. Portions of display 419 may be clearer than other portions or completely clear to enable the messages to be viewed. In embodiments having an overlay with varying clarity, the movable components may be moved from a position beneath a more opaque section of the overlay (in which position the movable component is not visible or less visible) to a position beneath a less opaque section (in which position the movable component is visible or more visible). In such a configuration, rather than moving a movable component toward and away from the overlay (in a vertical direction, in the orientation of FIG. 8), the movable components may instead be moved in a plane parallel to the overlay, between an opaque section of the overlay and a less opaque section. For example, in the condition shown in FIG. 8, movable component 441 is visible through a less opaque portion of the overlay, while movable component 443 (which may be positioned at the same height as movable component 441) is not visible (or less visible) through an opaque portion of the overlay. The positions of the movable components 441 and 443 may be changed (e.g., by being moved through a horizontal plane) to render only component 443 visible, to render both components 441 and 443 visible, or to render neither component visible.

Figure 9:
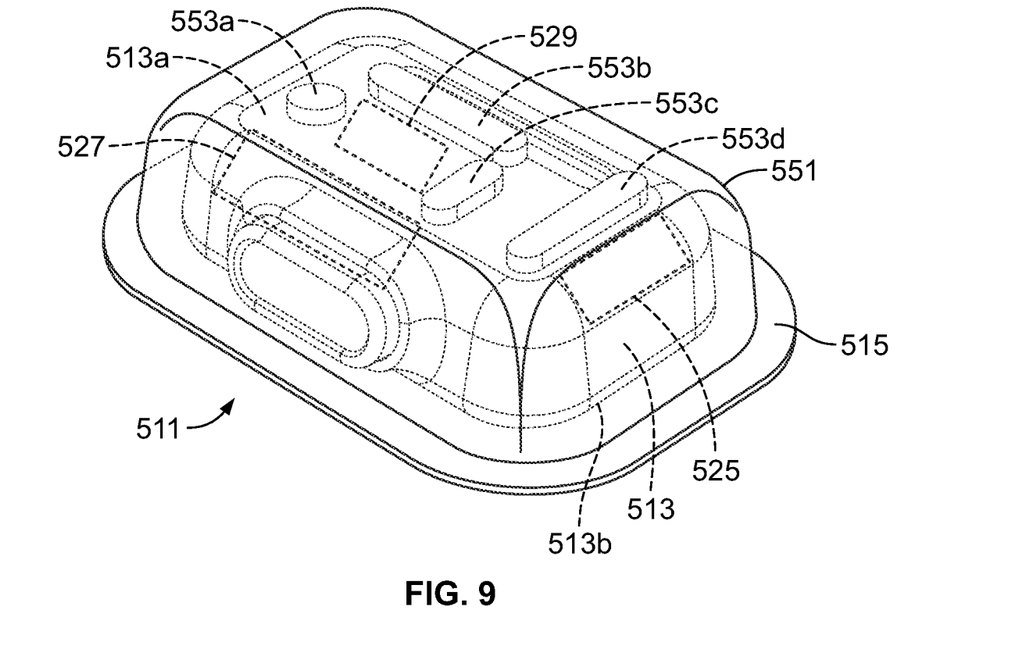
FIG. 9 is a top perspective view of a fifth exemplary embodiment of a drug delivery device with an improved display, according to an aspect of the present disclosure.
Figure 10:
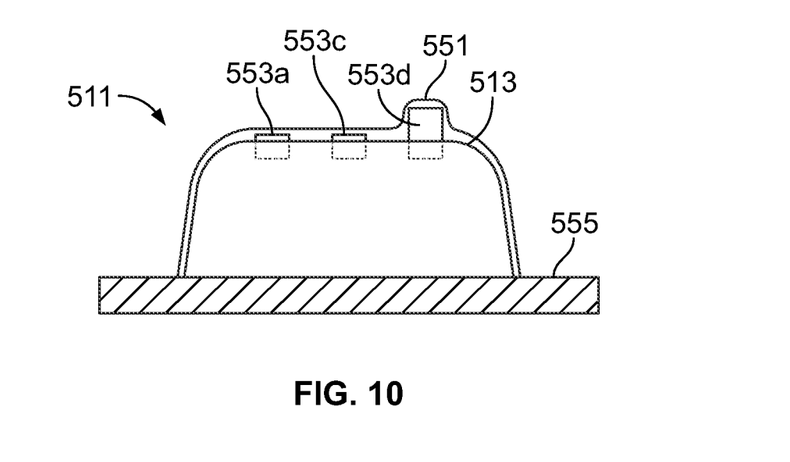
FIG. 10 is a side elevational view of the drug delivery device of FIG. 9.

FIGS. 9 and 10 show an exemplary device with a mechanical display having a cover layer 551. The cover layer may be flexible and/or deformable, rather than generally rigid (as is the case of the overlays of the embodiments of FIGS. 6-8). The cover layer may be deformed differently by movable components to indicate a status to the user. In order to deform the cover layer, a movable component must be moved into engagement with the cover layer, which may include a portion of the movable component being moved outside of the housing of the device (while still being shielded from the outside environment by the cover layer). Movable components 553a-553d are shown as being selectively movable by associated adjustment mechanisms to press against and deform cover layer 551. Components 553a-553d can be moved at once or at different times, depending on the message to be communicated to the user. The combination of components may present a message in Braille or provide some other type of tactile indication. The movable components may be differently sized and shaped or be a consistent size and shape. The movable components may be disposed on top of the device housing on the upper surface (beneath the cover layer) or at least partially within the device housing.

A drug delivery device having a deformable cover layer may be advantageous for patients having limited eyesight, as the message is conveyed tactilely, rather than visually (though the deformed cover layer may also be looked at to understand the message being presented). Additionally, it is possible for the device to be mounted to a body surface that is not readily visible (e.g., due to being covered by clothing), in which case deformation of the cover layer may be more readily perceived than the change of the visibility of a movable component positioned beneath a generally rigid overlay (as in the embodiments of FIGS. 6-8).

While different embodiments are shown and described separately, it is again emphasized that a single display may combine the features of two or more of the displays described (e.g., an electrical aspect and a mechanical aspect). It is also within the scope of the present disclosure for a single device to include a plurality of displays of the type described herein and/or to be provided in combination with traditional means for alerting a user (e.g., simple lights or buzzers).

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A drug delivery device comprising:
a housing including upper and lower surfaces;

an adhesive pad associated with the lower surface of the housing and configured to removably attach to a human body surface;
a drug reservoir positioned within the housing;
a needle fluidically connected to the drug reservoir and configured to define at least a portion of a fluid flow path between the drug reservoir and said human body surface;
a controller configured to execute a drug delivery routine;
a movable display positioned within the housing; and
an electromechanically actuatable adjustment mechanism coupled to the controller, wherein
the upper surface of the housing defines an overlay,
the controller is configured to control the adjustment mechanism to move the movable display with respect to the overlay from a first position to a second position, and
at least a portion of the movable display is visible through the overlay when the movable display is in one of said positions and said at least a portion of the movable display is differently visible or invisible through the overlay when the movable display is in the other one of said positions.

2. The drug device of claim 1, wherein the movable display is invisible or less visible in the first position.

3. The drug delivery device of claim 1, wherein the movable display is invisible or less visible in the second position.

4. The drug delivery device of claim 1, wherein the movable display is movable between the first and second positions.

5. The drug delivery device of claim 1, configured to deliver a drug comprising pegfilgrastim.

6. The drug delivery device of claim 1, wherein the overlay is translucent or transparent.

7. The drug delivery device of claim 1, wherein the overlay is a rigid material.

8. The drug delivery device of claim 1, wherein the movable display is a mechanical display.

9. The drug delivery device of claim 1, wherein the controller is configured to control adjustment mechanism to cause the movable display to physically move with respect to the overlay during said drug delivery routine.

10. The drug delivery device of claim 1, wherein the movable display is closer to the overlay in the first position than in the second position.

11. A drug delivery device comprising:
a housing including upper and lower surfaces;
an adhesive pad associated with the lower surface of the housing and configured to removably attach to a human body surface;
a drug reservoir positioned within the housing;
a needle fluidically connected to the drug reservoir and configured to define at least a portion of a fluid flow path between the drug reservoir and said human body surface;
a controller configured to execute a drug delivery routine;
a movable display positioned within the housing; and
an adjustment mechanism comprising a screw coupled to the controller, wherein
the upper surface of the housing defines an overlay,
the controller is configured to control the adjustment mechanism to move the movable display with respect to the overlay from a first position to a second position, and
at least a portion of the movable display is visible through the overlay when the movable display is in one of said positions and said at least a portion of the movable display is differently visible or invisible through the overlay when the movable display is in the other one of said positions.

12. A drug delivery device comprising:
a housing including upper and lower surfaces;
an adhesive pad associated with the lower surface of the housing and configured to removably attach to a human body surface;
a drug reservoir positioned within the housing;
a needle fluidically connected to the drug reservoir and configured to define at least a portion of a fluid flow path between the drug reservoir and said human body surface;
a controller configured to execute a drug delivery routine;
a movable display positioned within the housing; and
an adjustment mechanism comprising a cam coupled to the controller, wherein
the upper surface of the housing defines an overlay,
the controller is configured to control the adjustment mechanism to move the movable display with respect to the overlay from a first position to a second position, and
at least a portion of the movable display is visible through the overlay when the movable display is in one of said positions and said at least a portion of the movable display is differently visible or invisible through the overlay when the movable display is in the other one of said positions.

13. A drug delivery device comprising:
a housing including upper and lower surfaces;
an adhesive pad associated with the lower surface of the housing and configured to removably attach to a human body surface;
a drug reservoir positioned within the housing;
a needle fluidically connected to the drug reservoir and configured to define at least a portion of a fluid flow path between the drug reservoir and said human body surface;
a controller configured to execute a drug delivery routine; and
a movable display positioned within the housing comprising at least two movable components that are independently movable, wherein
the upper surface of the housing defines an overlay,
the controller is configured to control the movable display to move with respect to the overlay from a first position to a second position,
at least a portion of the movable display is visible through the overlay when the movable display is in one of said positions and said at least a portion of the movable display is differently visible or invisible through the overlay when the movable display is in the other one of said positions, and
the controller is configured to control the movable display to move with respect to the overlay such that no more than one of said at least two movable components is visible through the overlay at any time.

14. The drug delivery device of claim 13, wherein said at least two movable components have different sizes and/or shapes.

15. The drug delivery device of claim 13, wherein said at least two movable components have the same size and/or shape.

16. The drug delivery device of claim 13, wherein said at least two movable components are configured to be visible when positioned adjacent to the overlay.

17. The drug delivery device of claim 13, wherein said at least two movable components are configured to invisible when spaced away from the overlay.

\* \* \* \* \*